(12) United States Patent
Robinson

(10) Patent No.: US 7,479,292 B2
(45) Date of Patent: Jan. 20, 2009

(54) HAIR POMADE COMPOSITION AND METHOD OF MAKING THE SAME

(76) Inventor: Dixie Robinson, 9552 Gierson Ave., Chatsworth, CA (US) 91311

( * ) Notice: Subject to any disclaimer, the term of this patent is extended or adjusted under 35 U.S.C. 154(b) by 0 days.

(21) Appl. No.: 12/061,815

(22) Filed: Apr. 3, 2008

(65) Prior Publication Data

US 2008/0247983 A1   Oct. 9, 2008

Related U.S. Application Data

(60) Provisional application No. 60/910,111, filed on Apr. 4, 2007.

(51) Int. Cl.
*A61K 36/14* (2006.01)
*A61K 36/53* (2006.01)
*A61K 36/67* (2006.01)
*A61K 36/752* (2006.01)

(52) U.S. Cl. .................. 424/734; 424/758; 424/770; 424/776; 424/745; 424/736; 424/70.1

(58) Field of Classification Search ................... None
See application file for complete search history.

(56) References Cited

U.S. PATENT DOCUMENTS

| 4,002,734 A * | 1/1977 | Pickford .................. 424/74 |
| 6,582,736 B2 | 6/2003 | Quezada |
| 7,264,639 B2 | 9/2007 | Carrascal et al. |

* cited by examiner

*Primary Examiner*—Susan C Hoffman
(74) *Attorney, Agent, or Firm*—Kelly Lowry & Kelley, LLP

(57) ABSTRACT

The method for making a hair pomade composition includes the steps of melting petroleum jelly over a heated surface and then mixing sesame seed oil, meadowfoam seed oil, pumpkin seed oil, Cyprus oil, basil sweet oil, Rosemary oil, black pepper oil, lemon oil, and Anise oil with the melted petroleum jelly into a mixture. Thereafter, the all-natural hair pomade mixture is solidified.

17 Claims, No Drawings

HAIR POMADE COMPOSITION AND METHOD OF MAKING THE SAME

BACKGROUND OF THE INVENTION

The present invention is generally directed to a hair pomade composition and method of making the same. More particularly, the present invention relates to a method for making an all-natural hair pomade composition for nourishing the hair, promoting hair growth, cleansing and stimulating the scalp, detangling the hair, conditioning and glossing the hair, preventing and eliminating dandruff and cleansing pores.

Hairstyling and treatment compositions may include a variety of products including hairsprays, hair gels, hair glues, creams, mousse, and pomades. All of these hairstyling compositions typically include several active ingredients that give hair certain properties and styling characteristics. The hairstyle products are generally prepared for topical applications to the hair and skin.

Hairsprays or hair lacquers are aqueous solutions that are used to style hair or keep hair stiff. Hairsprays are weaker than hair gel, hair wax, or hair glue. Hairsprays typically require an aerosol spray nozzle, which function by omitting pressurized vapor such as chlorofluorocarbons (CFCs). Since the Montreal Protocol took effect Jan. 1, 1989, CFCs were replaced by other potentially harmful and extremely flammable hydrocarbons that include propane, n-butane, isobutene, dimethyl ether, and methylethyl ether.

The active ingredient in hairsprays is typically an artificial polymer, such as the chemical elastesse. The artificial polymers are a form of liquid elastic that keeps hair stiff and firm by lowering the amount of minerals in the hair root. Hairsprays are also scented.

Hair gel, like hairsprays, is a hairstyling product that also stiffens hair. Hair gel is typically stronger than hairspray and weaker relative to hair glue or hair wax. Hair gel styling is similar to the above-mentioned products in most respects. Additionally, hair mousse is available as either a cream or spray and is added to hair for extra volume and shine. When combined with hair gel, hair mousse creates a smooth, stiff, and wet look.

Also included in traditional hairstyling products are pomades, waxes, glues, and clays. Pomades are typically substances that facilitate hairstyling to improve control and appearance of the hair. Unlike hairsprays and hair gels, pomades do not dry. But, pomades increase the luster and hold of hair and may make the hair look slick and shiny.

Pomades are usually topically applied to hair in the form of an emulsion or a gel. Most pomades contain some form of petroleum jelly, a high proportion of water-insoluble materials, and a semi-solid mixture of hydrocarbons that continually absorbs moisture from the air and produces a feeling of wetness on the skin or hair. Other pomade ingredients might include a variety of waxes and artificially manufactured substances such as polyethylene glycol or ethyl hexanediol. Pomades, like other hairstyling products, may contain artificially scented perfumes, fruity fragrances, and coloring agents.

Accordingly, there is a need for an all-natural pomade. Such a pomade should include all-natural ingredients such as 100% pure petroleum jelly, sesame seed oil, meadowfoam seed oil, pumpkin seed oil, Cypress oil, basil sweet oil, Rosemary oil, black pepper oil, lemon oil, and Anise Oil to nourish, clean, stimulate, detangle, condition, gloss, and promote hair growth, while also preventing and eliminating dandruff. To add color to the pomade, the all-natural ingredients of benzoin, alkanet root, and citronella oil should also be added. The present invention fulfills these needs and provides further related advantages.

SUMMARY OF THE INVENTION

One embodiment of the present invention is directed to a method for making an all-natural hair pomade composition. The method for making the all-natural hair pomade composition includes the step of melting petroleum jelly over a heated surface. Preferably, the petroleum jelly comprises pure petroleum jelly. Optionally, alkanet root is added to the petroleum jelly to perform the step of coloring the resultant hair pomade composition. The alkanet root may be strained from the petroleum jelly prior to the step of solidifying the mixture. Next, a set of ingredients that include sesame seed oil, meadowfoam seed oil, pumpkin seed oil, Cypress oil, basil sweet oil, Rosemary oil, black pepper oil, lemon oil, and Anise oil are mixed with the melted petroleum jelly. In an alternative embodiment, benzoin and citronella oil are also mixed into the petroleum jelly mixture with the aforementioned all-natural ingredients. Preferably, the mixture is blended with a cake mixer. The mixture is thereafter solidified. The solidifying step may include the steps of pouring the mixture into a jar, cooling the mixture in the jar and covering the jar with a lid. The all-natural hair pomade composition is ready for application once it cools in the jar. Alternatively, the above-identified ingredients may be mixed and matched in any combination according to the steps described above.

The present invention is also directed to an all-natural hair pomade composition itself. The hair pomade composition comprises a solidified mixture of petroleum jelly in the range of 64%-74% by volume of the mixture, sesame seed oil in the range of 16%-21% by volume of the mixture, meadowfoam seed oil in the range of 0.1%-2.0% by volume of the mixture, pumpkin seed oil in the range of 0.1%-2.0% by volume of the mixture, Cyprus oil in the range of 0.05%-0.20% by volume of the mixture, basil sweet oil in the range of 0.6%-0.9% by volume of the mixture, Rosemary oil in the range of 2.0%-2.5% by volume of the mixture, black pepper oil in the range of 0.4%-0.7% by volume of the mixture, lemon oil in the range of 1.0%-1.3% by volume of the mixture and Anise oil in the range of 0.1%-0.3% by volume of the mixture. Alternatively, the composition may further include alkanet root in the range of 8%-10% by volume of the mixture. In another embodiment, the mixture further includes benzoin in the range of 0.2%-0.5% by volume of the mixture and citronella oil in the range of 0.2%-0.5% by volume of the mixture. Preferably, the petroleum jelly comprises pure petroleum jelly.

In an alternative embodiment, the petroleum jelly comprises 72%-73%, the sesame seed oil comprises 19%-20%, the meadowfoam seed oil comprises 1%-2%, the pumpkin seed oil comprises 1%-2%, the Cyprus oil comprises 0.10%-0.20%, the basil sweet oil comprises 0.8%-0.9%, the Rosemary oil comprises 2.4%-2.5%, the black pepper oil comprises 0.6%-0.7%, the lemon oil comprises 1.2%-1.3% and the Anise oil comprises 0.1%-0.3% by volume of the mixture.

In another alternative embodiment of the hair pomade composition of the present invention, the petroleum jelly comprises 66%-67%, the sesame seed oil comprises 17%-18%, the meadowfoam seed oil comprises 1.1%-1.2%, the pumpkin seed oil comprises 1.1%-1.2%, the Cyprus oil comprises 0.05%-0.10%, the basil sweet oil comprises 0.7%-0.8%, the Rosemary oil comprises 2.2%-2.3%, the black pepper oil comprises 0.5%-0.6%, the lemon oil comprises 1.1%-1.2%, the Anise oil comprises 0.1%-0.2% and the alkanet root comprises 8%-9% by volume of the mixture.

The all-natural hair pomade composition of the present invention may also alternatively include petroleum jelly comprising 65%-66%, sesame seed oil comprising 17%-18%, meadowfoam seed oil comprising 1.0%-1.2%, pumpkin seed oil comprising 1.0%-1.2%, Cyprus oil comprising 0.05%-0.10%, basil sweet oil comprising 0.7%-0.8%, Rosemary oil comprising 2.2%-2.3%, black pepper oil comprising 0.5%-0.6%, lemon oil comprising 1.1%-1.2%, Anise oil comprising 0.1%-0.2%, benzoin comprising 0.3%-0.4%, citronella oil comprising 0.3%-0.4% and alkanet root comprising 8%-9% by volume of the mixture.

In yet another alternative embodiment, the hair pomade composition of the present invention includes petroleum jelly comprising 72%-73%, sesame seed oil comprising 19%-20%, meadowfoam seed oil comprising 1.1%-1.3%, pumpkin seed oil comprising 1.1%-1.3%, Cyprus oil comprising 0.05%-0.10%, basil sweet oil comprising 0.8%-0.9%, Rosemary oil comprising 2.4%-2.5%, black pepper oil comprising 0.6%-0.7%, lemon oil comprising 1.2%-1.3%, Anise oil comprising 0.1%-0.3%, benzoin comprising 0.3%-0.5% and citronella oil comprising 0.3%-0.5% by volume of the mixture.

Accordingly, the hair pomade of the present invention could include any combination of the above described embodiments. All of the above-identified ingredients could be mixed and matched depending on the desired effect of the hair pomade. Most notably, any combination of the above-identified ingredients produces an all-natural hair pomade.

Other features and advantages of the present invention will become apparent from the following more detailed description.

DETAILED DESCRIPTION OF THE PREFERRED EMBODIMENTS

The hair pomade composition and method for making the same of the present invention comprises only all-natural ingredients, including plant oil extracts. In a preferred embodiment of the present invention, the hair pomade composition includes 30 ounces (oz.) of 100% pure petroleum jelly, 8 oz. of sesame seed oil, 1 tablespoon (tbsp.) of meadowfoam seed oil, 1 tbsp. of pumpkin seed oil, ¼ teaspoon (tsp.) of Cypress oil, 10 cubic centimeters (cc) of basil sweet oil, 30 cc of Rosemary oil, 7.5 cc of black pepper oil, 15 cc of lemon oil and ½ tsp. of Anise oil.

In an alternative embodiment of the present invention, the hair pomade further includes 1 tsp. of benzoin, ½ cup alkanet root and 1 tsp. citronella oil. In this embodiment, the alkanet root provides the hair pomade with a range of coloration. Addition of the alkanet root colors the hair pomade product, not the hair itself. The benzoin is used to preserve the alkanet root while the citronella oil eliminates any unpleasant odors from the alkanet root.

The 100% pure petroleum jelly is the base of the hair pomade and is used to carry the remaining ingredients. The 100% pure petroleum jelly holds the mixture, including the aforementioned oils, in solid form once the mixture cools and solidifies. The protein rich 100% pure petroleum jelly may also sooth and soften rough or dry skin. The sesame seed oil is used to prevent the 100% pure petroleum jelly from becoming too heavy or greasy when applied in topical form to the hair. The sesame seed oil also acts as an antibacterial for common skin pathogens, an antiviral, and an anti-inflammatory agent. The meadowfoam seed oil is an oil moisturizer for the scalp and also provides nourishment for the hair. Meadowfoam seed oil penetrates and repairs human hair fibers upon application and also helps add shine.

Additional oils may be added to the all-natural hair pomade composition to derive additional benefits from application. For example, the pumpkin seed oil is rich in zinc and nourishes and promotes hair growth. The Cypress oil is a scalp stimulant and scalp cleanser. The basil sweet oil promotes hair growth and detangles the hair. The Rosemary oil conditions the hair and provides an exterior gloss to make the hair shiny. The black pepper oil provides a spicy aroma. Additionally, the black pepper oil provides a warm tingling sensation to the scalp which lasts for a few seconds after the hair pomade is applied to the scalp. The black pepper oil is also a hair stimulator.

Additionally, lemon oil is included to prevent and eliminate dandruff. The Anise oil is used to open up and cleanse the pores of the scalp. Benzoin is a natural preservative for the alkanet root. The alkanet root is used in traditional crafts as a dye. Alkanet root has red bark that soaked with the 100% pure petroleum jelly to dye the hair pomade red. The length of time the alkanet root is soaked in the 100% pure petroleum jelly solution determines the color of the hair pomade. Initially, the hair pomade is light pink and can range to a deep ruby red the longer the alkanet root soaks in the solution. The alkanet root only dyes the hair pomade product and not the hair. The alkanet root is an all-natural product coloration agent. Additionally, upon application, users will not experience a change in hair color even when applying a deep ruby red hair pomade. The hair pomade, regardless of coloration, is clear in application. Lastly, the citronella oil gives the hair a lustrous shine and eliminates any unpleasant odors associated with the alkanet root.

Any combination of the above described ingredients could be used to make the hair pomade of the present invention. In one alternative embodiment, the amount of 100% pure petroleum jelly relative to the amount of sesame seed oil could be varied depending on the desired thickness and greasiness of the hair pomade. In another alternative embodiment, if coloration of the hair pomade is not desired, the alkanet root would not be added. Accordingly, the benzoin and citronella oil would not be needed to preserve or eliminate any unpleasant odor from the alkanet root, respectively.

In another additional embodiment, the meadowfoam seed oil could be excluded if moisturization of the scalp is not required and limited hair nourishment is needed. Alternatively, the pumpkin seed oil could be excluded from the hair pomade if further nourishment and hair growth is not required. In yet another alternative embodiment, the Cypress oil could be excluded if a scalp stimulant and cleanser are not required. In still yet another alternative embodiment, the basil sweet oil could be excluded if the hair pomade does not require hair detanglement or require as much hair growth. In another alternative embodiment, the Rosemary oil could be excluded if the hair pomade does not need to condition or gloss the hair. In a further alternative embodiment, the black pepper oil could be excluded if a spicy aroma or warm tingling sensation upon application is not required or desired. Moreover, the lemon oil could be excluded from the hair pomade if dandruff does not need to be eliminated or prevented. In an alternative embodiment, the citronella oil could be excluded from the hair pomade composition if it were not desired to eliminate the odor from the alkanet root or if the alkanet root was not added during the process of making the hair pomade composition. In yet another alternative embodiment, the hair pomade may exclude the Anise oil, in which the hair pomade would not open and cleanse the pores of the scalp. Each one of the above-described ingredients could be mixed and matched depending on the desired effect of the hair pomade upon application. Most notably, the hair pomade, in any combination of the above-described embodiments, remains all-natural.

The quantity of each ingredient can be varied pending the relative ratios among all the ingredients stays constant. For example, in the embodiment previously described, the hair pomade includes 30 oz. of 100% pure petroleum jelly, 8 oz. of sesame seed oil, etc. To make a batch of hair pomade that is twice as large, 60 oz. of 100% pure petroleum, 16 oz. of sesame seed oil, etc. is needed. Note that the quantity of all ingredients will double if a batch twice the already described embodiment is desired. Any size batch is obtainable with these relative quantities.

In the preferred embodiment for the method of manufacturing the hair pomade composition of the present invention, the 100% pure petroleum jelly is placed into an enamel pot. The enamel pot is placed over a low heating stove burner to melt the 100% pure petroleum jelly. Once the 100% pure petroleum jelly is melted, the desired quantity of alkanet root is then mixed therein. The combination of the 100% pure petroleum jelly and alkanet root is allowed to heat together. The color of the mixture will vary from an initial light pinkish color to a deep ruby red depending upon the length of time that the alkanet root is soaked in the 100% pure petroleum jelly over the heat from the stove burner. The hair pomade takes on a deeper red color the longer the alkanet root soaks in the mixture.

At this point, the alkanet roots are optionally strained out from the 100% pure petroleum jelly before the combinations of oils are added. Once the alkanet roots are removed, the desired oils, such as the sesame seed oil, meadowfoam seed oil, pumpkin seed oil, Cypress oil, basil sweet oil, Rosemary oil, black pepper oil, lemon oil, Anise oil, benzoin, and citronella oil are poured into the enamel pot with the melted 100% pure petroleum jelly and any dye extracted from the alkanet root. The combination of the oils and the 100% pure petroleum jelly are then blended with a cake mixer. Any one of a number of different mixers that accomplishes the same or similar functionality as a cake mixer could be used with the present invention. The important aspect is that the ingredients (i.e., the 100% pure petroleum jelly and various oils) are homogenously mixed together.

Once the 100% pure petroleum jelly and various oils are properly mixed, the entire solution is poured into a series of plastic jars. The hair pomade is allowed to cool and solidify in the plastic jars. As a final step, each jar is covered and secured with a top. The hair pomade is then ready for use. Upon application, the hair pomade goes on clear.

In an alternative embodiment the alkanet roots are not removed before the desired all-natural oils are added to the hair pomade. In this embodiment, the alkanet root are homogenously mixed into the hair pomade and thereafter do not require straining before the entire solution is poured into a series of jars as described in the preceding paragraph.

Further alternative embodiments of the method for manufacturing the hair pomade of the present invention include any of the previously described combination of ingredients. In these embodiments, the only difference is the ingredients are placed into the enamel pot before mixing. The desired ingredients may be added in any order.

Although several embodiments have been described in detail for purposes of illustration, various modifications may be made without departing from the scope and spirit of the invention. Accordingly, the invention is not to be limited, except as by the appended claims.

What is claimed is:

1. A method for making a hair pomade composition, comprising the steps of:
    melting petroleum jelly;
    mixing sesame seed oil, meadowfoam seed oil, pumpkin seed oil, Cypress oil, basil sweet oil, Rosemary oil, black pepper oil, lemon oil and Anise oil with the melted petroleum jelly into a mixture; and
    solidifying the mixture.

2. The method of claim 1, including the step of adding alkanet root to the melted petroleum jelly.

3. The method of claim 2, including the step of straining the alkanet root from the petroleum jelly prior to the step of solidifying the mixture.

4. The method of claim 2, including the step of coloring the melted petroleum jelly with the alkanet root.

5. The method of claim 1, wherein the mixing step includes the step of mixing benzoin and citronella oil into the mixture.

6. The method of claim 1, wherein the mixing step includes the step of blending the mixture with a cake mixer.

7. The method of claim 1, wherein the petroleum jelly comprises 100% pure petroleum jelly.

8. The method of claim 1, wherein the solidifying step comprises the steps of:
    pouring the mixture into a jar;
    cooling the mixture in the jar; and
    covering the jar with a lid.

9. A hair pomade composition, comprising:
    a solidified mixture of petroleum jelly in the range of 64%-74% by volume of the mixture, sesame seed oil in the range of 16%-21% by volume of the mixture, meadowfoam seed oil in the range of 0.1%-2.0% by volume of the mixture, pumpkin seed oil in the range of 0.1%-2.0% by volume of the mixture, Cypress oil in the range of 0.05%-0.20% by volume of the mixture, basil sweet oil in the range of 0.6%-0.9% by volume of the mixture, Rosemary oil in the range of 2.0%-2.5% by volume of the mixture, black pepper oil in the range of 0.4%-0.7% by volume of the mixture, lemon oil in the range of 1.0%-1.3% by volume of the mixture and Anise oil in the range of 0.1%-0.3% by volume of the mixture.

10. The composition of claim 9, wherein the petroleum jelly comprises 100% pure petroleum jelly.

11. The composition of claim 9, wherein the petroleum jelly comprises 72%-73%, the sesame seed oil comprises 19%-20%, the meadowfoam seed oil comprises 1%-2%, the pumpkin seed oil comprises 1%-2%, the Cypress oil comprises 0.10%-0.20%, the basil sweet oil comprises 0.8%-0.9%, the Rosemary oil comprises 2.4%-2.5%, the black pepper oil comprises 0.6%-0.7%, the lemon oil comprises 1.2%-1.3% and the Anise oil comprises 0.1%-0.3% by volume of the mixture.

12. The composition of claim 9, including alkanet root in the range of 8%-10% by volume of the mixture.

13. The composition of claim 12, wherein the petroleum jelly comprises 66%-67%, the sesame seed oil comprises 17%-18%, the meadowfoam seed oil comprises 1.1%-1.2%, the pumpkin seed oil comprises 1.1%-1.2%, the Cypress oil comprises 0.05%-0.10%, the basil sweet oil comprises 0.7%-0.8%, the Rosemary oil comprises 2.2%-2.3%, the black pepper oil comprises 0.5%-0.6%, the lemon oil comprises 1.1%-1.2%, the Anise oil comprises 0.1%-0.2% and the alkanet root comprises 8%-9% by volume of the mixture.

14. The composition of claim 12, including benzoin in the range of 0.2%-0.5% by volume of the mixture and citronella oil in the range of 0.2%-0.5% by volume of the mixture.

15. The composition of claim 14, wherein the petroleum jelly comprises 65%-66%, the sesame seed oil comprises 17%-18%, the meadowfoam seed oil comprises 1.0%-1.2%, the pumpkin seed oil comprises 1.0%-1.2%, the Cypress oil comprises 0.05%-0.10%, the basil sweet oil comprises 0.7%-0.8%, the Rosemary oil comprises 2.2%-2.3%, the black pepper oil comprises 0.5%-0.6%, the lemon oil comprises 1.1%-1.2%, the Anise oil comprises 0.1%-0.2%, the benzoin comprises 0.3%-0.4%, the citronella oil comprises 0.3%-0.4% and the alkanet root comprises 8%-9% by volume of the mixture.

16. The composition of claim 9, including benzoin in the range of 0.2%-0.5% by volume of the mixture and citronella oil in the range of 0.2%-0.5% by volume of the mixture.

17. The composition of claim 16, wherein the petroleum jelly comprises 72%-73%, the sesame seed oil comprises 19%-20%, the meadowfoam seed oil comprises 1.1%-1.3%, the pumpkin seed oil comprises 1.1%-1.3%, the Cypress oil comprises 0.05%-0.10%, the basil sweet oil comprises 0.8%-0.9%, the Rosemary oil comprises 2.4%-2.5%, the black pepper oil comprises 0.6%-0.7%, the lemon oil comprises 1.2%-1.3%, the Anise oil comprises 0.1%-0.3%, the benzoin comprises 0.3%-0.5% and the citronella oil comprises 0.3%-0.5% by volume of the mixture.

* * * * *